United States Patent
Jordan et al.

(10) Patent No.: US 8,983,535 B2
(45) Date of Patent: Mar. 17, 2015

(54) MEDICAL SCAN CLIP ON

(75) Inventors: Connie Jordan, Laguna Niguel, CA (US); Christopher Carmichael, Laguna Niguel, CA (US)

(73) Assignee: Ubiquity Broadcasting Corporation, Irvine, CA (US)

( * ) Notice: Subject to any disclaimer, the term of this patent is extended or adjusted under 35 U.S.C. 154(b) by 0 days.

(21) Appl. No.: 12/753,895

(22) Filed: Apr. 4, 2010

(65) Prior Publication Data

US 2010/0255876 A1 Oct. 7, 2010

Related U.S. Application Data

(60) Provisional application No. 61/166,674, filed on Apr. 3, 2009.

(51) Int. Cl.
| | |
|---|---|
| *H04M 1/00* | (2006.01) |
| *A61B 5/00* | (2006.01) |
| *G06F 19/00* | (2011.01) |
| *A61B 5/021* | (2006.01) |
| *A61B 5/024* | (2006.01) |
| *H04M 1/21* | (2006.01) |

(52) U.S. Cl.
CPC .......... *A61B 5/0002* (2013.01); *G06F 19/3418* (2013.01); *A61B 5/6898* (2013.01); *A61B 5/021* (2013.01); *A61B 5/024* (2013.01); *H04M 1/21* (2013.01); *A61B 2560/0443* (2013.01); *A61B 2560/0406* (2013.01)

USPC .................... 455/556.1; 455/557; 455/575.1; 455/66.1; 455/556.2; 455/67.11; 455/550.1

(58) Field of Classification Search
CPC ... H04M 1/21; G06F 19/3418; A61B 5/0002; A61B 5/6898
USPC .............. 455/556.1, 557, 575.1, 66.1, 556.2, 455/67.11, 550.1
See application file for complete search history.

(56) References Cited

U.S. PATENT DOCUMENTS

| | | | | |
|---|---|---|---|---|
| 8,599,014 | B2 * | 12/2013 | Prykari et al. | 340/540 |
| 2003/0036683 | A1 * | 2/2003 | Kehr et al. | 600/300 |
| 2008/0070599 | A1 * | 3/2008 | Apodaca et al. | 455/458 |
| 2008/0208015 | A1 * | 8/2008 | Morris et al. | 600/301 |
| 2008/0246629 | A1 * | 10/2008 | Tsui et al. | 340/870.07 |
| 2008/0266205 | A1 * | 10/2008 | Moehring | 345/1.2 |
| 2009/0115628 | A1 * | 5/2009 | Dicks et al. | 340/870.07 |
| 2009/0156199 | A1 * | 6/2009 | Steenstra et al. | 455/425 |
| 2011/0014954 | A1 * | 1/2011 | Dossas et al. | 455/566 |
| 2012/0290266 | A1 * | 11/2012 | Jain et al. | 702/187 |

\* cited by examiner

*Primary Examiner* — Barry Taylor
(74) *Attorney, Agent, or Firm* — Law Office of Scott C. Harris, In.

(57) ABSTRACT

Medical device that scans medical parameters and communicates via a cell phone. The cell phone can communicate the parameters to a remote location and/or or can analyze them. The medical device can be powered by the cell phone or can be wireless. A relatively large area for a pad that forms the surface area that determines the medical information can thus be obtained.

17 Claims, 2 Drawing Sheets

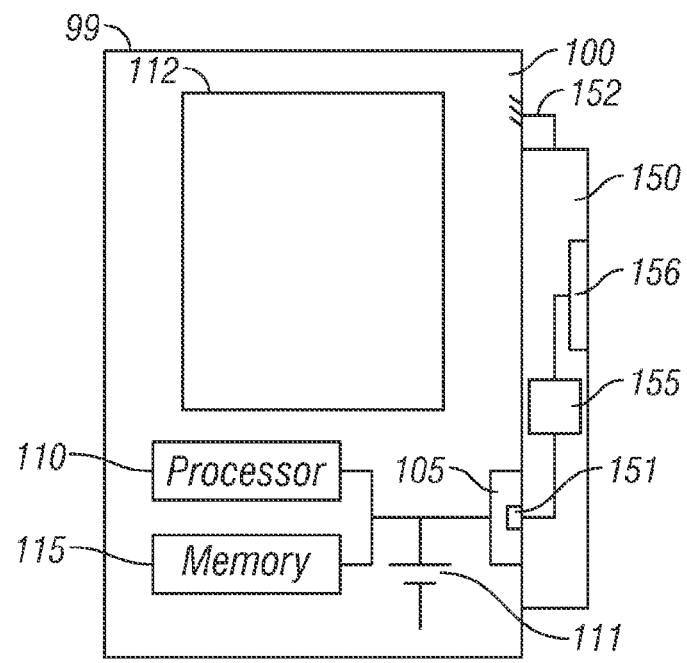
FIG. 1
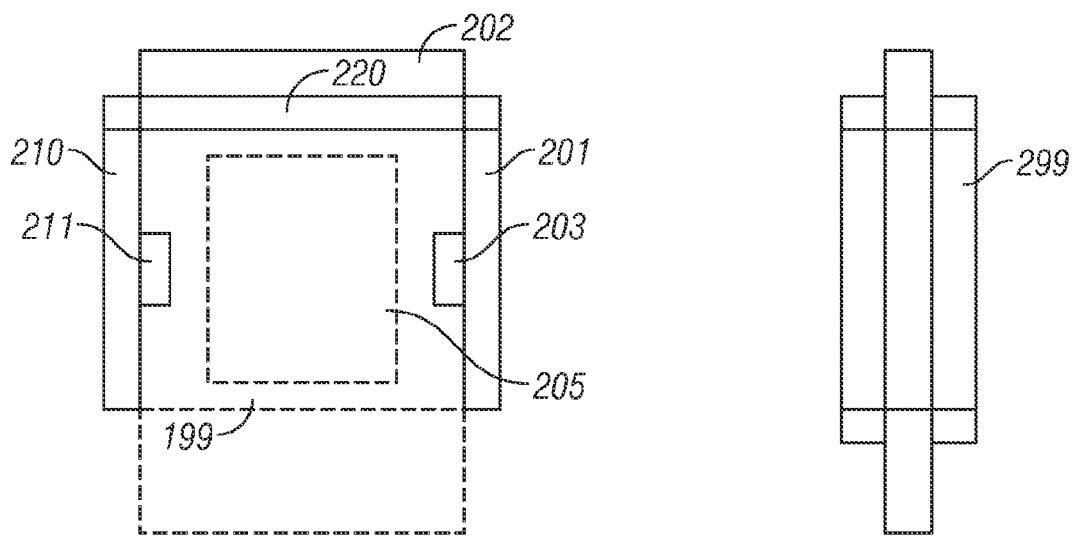
FIG. 2  FIG. 3

MEDICAL SCAN CLIP ON

This application claims priority from Provisional application No. 61/166,674, filed Apr. 3, 2009, the entire contents of which are herewith incorporated by reference.

BACKGROUND

Cell phones have become ubiquitous in the sense that most people carry cell phones with them as part of almost every activity. The convenience of the cell phone allows people to carry out functions from virtually anywhere, including making calls and saving their calendar.

Many functions are available for cell phones. Some of these functions are based on computer programs, or "apps" that use the computer within a cell phone to carry out some operation. The cell phone already has much data that it can use for this operation, and other data from the network connection of a cell phone, e.g., over the network connection.

SUMMARY

The inventors recognize that the cell phone is only able to process information for which it has data.

The present application describes a device which attaches to a cell phone, and retrieves medical data. The cell phone may process this data, or may pre-process the data, and then send this data to a remote location for processing and/or storage.

BRIEF DESCRIPTION OF THE DRAWINGS in the drawings:

FIG. 1 shows a phone or PDA with processing and connection;

FIG. 2 shows how the clip on devices clipped onto the PDA;

FIG. 3 shows a wireless medical monitor.

DETAILED DESCRIPTION

Figure 4:
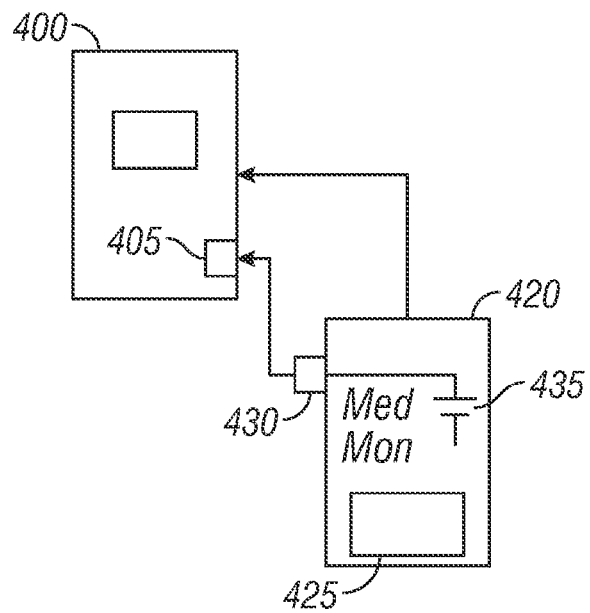
FIG. 4 shows an embodiment where the device is a medical monitor device.

The present application describes a clip on device, that attaches to a portable device, e.g., a phone or PDA.

One recognition is that while it is desirable to make cell phones as small as possible, certain monitoring devices may require certain surface area in order to operate properly. For example, a heartbeat electrode may require a certain amount of contact with the skin, causing it to have a certain required area. While you want to keep your cell phone small, the inventors recognize that monitoring of medical information may in fact require large surface areas to press against the user's skin in order to obtain accurate data.

According to one embodiment, the device is removable from the phone. This allows a large device, which can be removed from the phone, to make a smaller device. The larger areas carry out medical scanning functions.

The phone 99 is shown in FIG. 1. As conventional, the phone includes a casing 100 with at least one connection 105. For example, the connection 105 may be a USB style connection. That connection 105 allows charging power to be applied to the battery 111, and also acts as a data connection to receive and send data. For example, the phone may include a processor 110 which operates according to a stored program, and memory 115 for storing data, where the memory can be, e.g., RAM, flash memory, and/or other forms of optical and/or magnetic memory.

The connection 105 may get and receive data from the processor 110 and memory 115. The program may process this information, and information from the program can be displayed on screen 112.

According to one embodiment, the external device is a clip on device 150 for the phone 99. A first embodiment shown in FIG. 1 forms a clip on device with an electrical connector 151 that fits within the USB port 105, at a first end. The second end of the device includes housing clips 152 which attach to the outer surface of the housing 100. The clips can have inner surfaces, for example, which are moveable to press against the outer surface of the cell phone. The device itself can include circuitry such as 155 which is powered by power supplied over the USB port, and operates to communicate over the USB port 105. For example, in the embodiments described herein, this circuitry 155 can include medical monitoring circuitry.

The device can also include, for example, a monitoring pad 156 which can be used to acquire any medical information. For example, the monitoring pad 156 can be configured to include a variety of medical diagnostic instruments such as a heartbeat detector probe, a skin chemistry detector for diabetes, or a blood pressure sensor. The data gathered by a probe, detector, sensor, or the like will be available for viewing utilizing the phone screen. The phone will also store, process, and transmit this data.

In another embodiment, the device 199 can clip around the back of the phone as shown in FIG. 2, pressing against opposite outer surfaces of the phone as shown in FIG. 2. For example, the clip 201 may clip around one side 202 of the phone, and have a front clip portion 203 which touches a small portion of the front part of the phone to keep the clip 201 from falling off the phone once clipped on. The back portion 220 of the clip extends across the whole phone 99. This back portion is also slightly flexible, so that the distance between the two sides of the clip can be slightly open to remove the clip from the phone.

The second side of the clip is formed shown as 210, again with a front clip portion 211. Moreover, the portion 220 forms a large surface on which medical scanning pads, e.g., EKG pads/probes or skin based chemical detectors may be attached.

The device shown in FIG. 2 may also include a medical monitor part 205. In different embodiments, this can be a heart rate monitor, or pulse monitor or chemistry detector. It can obtain other kinds of electronic scans, for example a scan that analyzes and determines information about the amount of hemoglobin in the person's blood. Any kind of medical scanning that can be carried out by touching the person, can be carried out by the monitor 205.

In an embodiment shown in FIG. 3, the device can click around the side of the phone as an alternative, allowing a smaller part of the phone to be covered.

In any of these embodiments, the clips can be adjustable, so that the size between the different surfaces forming the clip can be adjusted. This allows the device to clip onto many different cellular phones. The clip adjustment may use, for example, a screw connection which sets the size between surfaces.

Another embodiment, shown in FIG. 4 uses a removable medical monitor device. The phone 400 has wireless communication capabilities such as by Bluetooth or WiFi. The phone 400 also includes a USB port 405. The medical monitor device 420 includes a medical monitoring pad 425 and also includes a USB connector 430. The USB connector can be connected to the corresponding USB connector in the phone 405. When operating in this way, the medical monitor operates in a wired connection, and also operates to charge the internal battery 435. However, the medical monitor can also be removed from the phone, with the part 430 removed from the USB port 405. When this happens, the device operates using the battery power from battery 435, to obtain information from the medical pad 425, and transfer it via wireless communication to the phone for example by Bluetooth or other wireless format or by a wired format.

Figure 5:
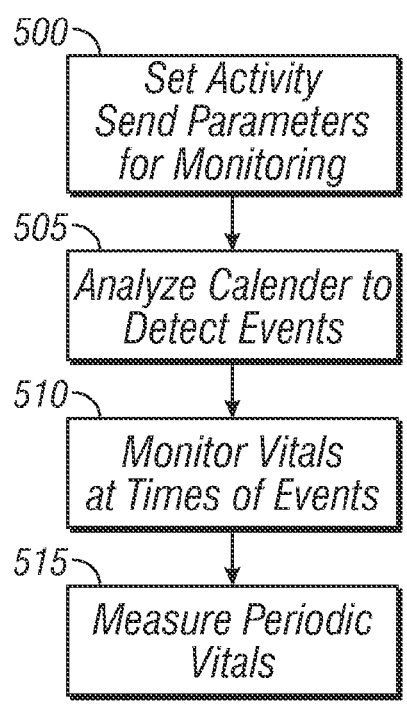
FIG. 5 shows a flowchart of operation.

The phone 100 may run a routine which can be a downloadable routine, or can be part of the phone, or associated with the portable device. The routine may be a program that operates using the processor 120, according to the flowchart of FIG. 5. One mode, shown as 500, defines setting an activity, and sending parameters for monitoring during that activity.

In one embodiment, an example is described relative to a user jogging. In the mode shown as 500, the user can send the medical information during jogging to for example their doctor, who can watch the parameters directly. Another program shown as 501 may analyze this data, to look for specified anomalies, for example an irregular heart rhythm. Responsive to detecting some specified kind of anomalies in the heart rhythm, the user can be warned about a heart sinus problem, or the data can be sent to a remote location as described above. This latter embodiment does local processing of the data on the phone, to find any data that might represent a problem. That pre-processed data is sent to the remote device for analysis e.g. to the doctor. In this embodiment, the phone processes the data and sends only some of the data to the remote location.

This system can also be used to store statistics at specified times in between visits to the doctor. In one embodiment, the device 99 can be a PDA, which can also keep track of events that occur in the owner's life at 505. For example, an owner can use their PDA to indicate which days they exercise. One statistic for example can indicate whether a user's blood pressure is reduced on the days they exercise.

Another alternative may use the calendar to monitor different kinds of meetings for example a performance review, meeting with client or any other kind of meeting. At 510 the system monitors body parameters at the times of the event. This allows determination of whether the body parameters change at the times of the events.

Another embodiment, shown in 515, simply measures the body parameters periodically, and either save or transmits these parameters, to provide a history of the body parameters.

Although only a few embodiments have been disclosed in detail above, other embodiments are possible and the inventors intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art. For example, other parameters can be monitored by this medical device, and the device can monitor parameters other than purely medical. Also, other kinds of data and phone connections can be used. For example, while this describes Bluetooth and USB connections, other wireless and wired connections can alternatively be used.

Also, input devices that can be "clipped on" to the wireless/mobile device. Those other devices may include, for example, photo/video cameras, document scanners, additional voice recording devices, 3D, holographic game consoles, or any other kind of device.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments of the invention.

The various illustrative logical blocks, modules, and circuits described in connection with the embodiments disclosed herein, may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has a user interface port that communicates with a user interface, and which receives commands entered by a user, has at least one memory (e.g., hard drive or other comparable storage, and random access memory) that stores electronic information including a program that operates under control of the processor and with communication via the user interface port, and a video output that produces its output via any kind of video output format, e.g., VGA, DVI, HDMI, displayport, or any other form.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Operations as described herein can be carried out on or over a website. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

Also, the inventors intend that only those claims which use the words "means for" are intended to be interpreted under 35 USC 112, sixth paragraph. Moreover, no limitations from the specification are intended to be read into any claims, unless those limitations are expressly included in the claims. The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Where a specific numerical value is mentioned herein, it should be considered that the value may be increased or decreased by 20%, while still staying within the teachings of the present application, unless some different range is specifically mentioned. Where a specified logical sense is used, the opposite logical sense is also intended to be encompassed.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A device, comprising:
a medical scanning part, having a first part with a surface that is used for a medical scan, where said medical scan is carried out by said surface touching a user, and said medical scanning part having a second part which communicates information indicative of the medical scan, said second part having circuitry that communicates with a cellular phone device that carries out a cellular phone function, and where the cellular phone includes a memory that stores calendar events including meeting times and information about a kind of event at said meeting times, and where the cellular phone obtains data indicative of said medical monitoring at times of said calendar events indicative of said meeting times, and said cellular phone includes a processor that correlates data indicative of medical monitoring data with said calendar events to determine and with said information indicative of meetings, and wherein the medical scanning part monitors to determine body parameters at times of the meetings including determining whether the body parameters change at the times of the different events,
and where the cellular phone includes a function to determine a day on which a user of the cellular phone has exercised, and to obtain a statistic based on said data indicative of said medical monitoring indicating whether the users body parameters change on days where the user has exercised.

2. A device as in claim 1, wherein said second part communicates via a wire connection to the cellular phone, over a port on the cellular phone, and where said port also provides power for at least one circuit in the medical scanning part.

3. A device as in claim 2, further comprising a battery in the medical scanning part, said battery being charged by power that is provided over said port.

4. A device as in claim 2, further comprising at least one clip, which clips the medical scanning part to outer surfaces of said cellular phone.

5. A device as in claim 4, wherein said at least one clip is adjustable for different outer surface sizes of different phones.

6. A device as in claim 1, wherein said second part communicates via wireless communication to the cellular phone.

7. A device as in claim 2, wherein said second part also communicates via a wireless communication to the cellular phone.

8. A device, comprising:
a portable phone having a call communicating function which allows sending and receiving calls over a cellular network and also controlling sending and receiving data over the cellular network;
a port which receives data, said port receiving medical data from an external sensor;
said portable phone having a processor running a program which analyzes said medical data, and where said program controls the sending of at least some of said medical data to a remote source over such a cellular network, depending on a condition, and where the cellular phone stores calendar events including meeting times, and where the cellular phone obtains data indicative of said medical monitoring data at times of said calendar events indicative of meeting times, and wherein said data indicative of medical monitoring data is correlated with said calendar events and with said information indicative of meetings, and wherein the medical scanning part monitors body parameters at times of the meetings, and where the portable phone includes a function to determine a day on which a user of the portable phone has exercised, and to obtain a statistic based on said medical data, indicating whether the users body parameters change on days where the user has exercised.

9. A device as in claim 8, wherein said condition is specified times when the parameters are monitored.

10. A device as in claim 8, wherein said meetings are meetings with another person other than the user of the portable phone.

11. A device as in claim 8, wherein said program analyzes said parameters to find at least one anomaly in said parameters, and sends only values that have such an anomaly over the cellular network.

12. A device as in claim 8, wherein said program analyzes heartbeat data.

13. A device as in claim 8, wherein said program analyzes blood chemistry data.

14. A method, comprising:
   using a cell phone for receiving data indicative of medical monitoring;
   using the cell phone for analyzing said medical monitoring data;
   using the cell phone for sending some but not all of the medical monitoring data to a remote location, based on said monitoring, where said monitoring determines some of the medical monitoring data to be sent, and said cell phone sends said data to be sent and where the cellular phone stores calendar events including meeting times, and where the cellular phone obtains data indicative of said medical monitoring data at times of said calendar events indicative of meeting times, and wherein said data indicative of medical monitoring data is correlated with said calendar events and with said information indicative of meetings, and wherein the medical scanning part monitors body parameters at times of the meetings, and where the cell phone includes a function to determine a day on which a user of the cell phone has exercised, and to obtain a statistic based on said data indicative of said medical monitoring indicating whether the user's body parameters change on days where the user has exercised.

15. A method as in claim 14, wherein said meetings are meetings with other people other than users of the cellular phone.

16. A method as in claim 14, wherein said medical monitoring data includes heartbeat data.

17. A method as in claim 14, wherein said medical monitoring data includes blood chemistry data.

\* \* \* \* \*